(12) United States Patent
Pitterna

(10) Patent No.: US 6,187,927 B1
(45) Date of Patent: Feb. 13, 2001

(54) PROCESS FOR PREPARING A 2-CHLORO-5-CHLOROMETHYL-THIAZOLE COMPOUND

(75) Inventor: Thomas Pitterna, Basel (CH)

(73) Assignee: Novartis Crop Protection, Inc., Greensboro, NC (US)

( * ) Notice: Under 35 U.S.C. 154(b), the term of this patent shall be extended for 0 days.

(21) Appl. No.: 09/029,642

(22) PCT Filed: Sep. 5, 1996

(86) PCT No.: PCT/EP96/03897

§ 371 Date: Mar. 6, 1998

§ 102(e) Date: Mar. 6, 1998

(87) PCT Pub. No.: WO97/10226

PCT Pub. Date: Mar. 20, 1997

(30) Foreign Application Priority Data

Sep. 11, 1995 (CH) .................................. 2570/95

(51) Int. Cl.⁷ ................................................. C07D 277/32
(52) U.S. Cl. ............................................................. 548/202
(58) Field of Search ............................................ 548/202

(56) References Cited

U.S. PATENT DOCUMENTS 4,748,243  5/1988  Beck et al. ........................... 548/202
5,180,833  1/1993  Uneme et al. ....................... 548/202

FOREIGN PATENT DOCUMENTS 2100924  1/1994  (CA) .

*Primary Examiner*—Robert Gerstl
(74) *Attorney, Agent, or Firm*—John D. Peabody, III; William A. Teoli, Jr.

(57) ABSTRACT

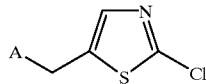

(I)

The invention relates to a process for preparing a compound of formula (I) in which A is chlorine or 3-methyl-4-nitroimino-perhydro-1,3,5-oxadiazin-5-yl; to intermediates used in this process; to the use of these intermediates; and to a process for the preparation of these intermediates. The compounds of formula (I) are valuable intermediates in the process of preparing pesticidal, especially insecticidal or acaricidal, formulations.

9 Claims, No Drawings

PROCESS FOR PREPARING A 2-CHLORO-5-CHLOROMETHYL-THIAZOLE COMPOUND

The invention relates to a process for preparing a known compound of the formula

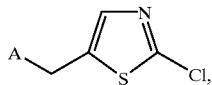
I in which A is chlorine or 3-methyl-4-nitroimino-perhydro-1,3,5-oxadiazin-5-yl, which process comprises a) reacting a compound of the formula

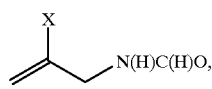
II in which X is a leaving group, if desired in the presence of a base, with a dehydrating agent, a halogenating agent and a sulfurizing agent to give the compound of the formula I, in which A is chlorine, or b1) reacting a compound of the formula II, if desired in the presence of a base, with a dehydrating agent to give a compound of the formula

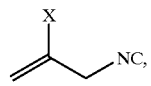
III in which X is as defined for the formula II, and b2) reacting the compound thus obtainable of the formula III with a halogenating agent and a sulfurizing agent, if desired in the presence of a base or acid, to give the compound of the formula I, in which A is chlorine, or c) reacting a compound of the formula

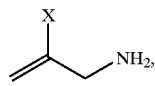
IV which is known or can be prepared in analogy to corresponding known compounds and in which X is as defined for the formula II, with a compound of the formula

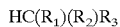
V, which is known or can be prepared in analogy to corresponding known compounds and in which either $R_1$ and $R_2$ together are oxo and $R_3$ is hydroxy, $C_1$–$C_6$alkoxy or $N(R_4)R_5$, $R_4$ and $R_5$ being, independently of one another, hydrogen or $C_1$–$C_6$alkyl, or $R_1$, $R_2$ and $R_3$, independently of one another, are $C_1$–$C_6$alkoxy, to give a compound of the formula II and reacting the compound thus obtainable of the formula II either in accordance with the process variant a) or in accordance with the process variant b1)/b2) to give the compound of the formula I, in which A is chlorine, or d) preparing the compound of the formula I in which A is chlorine, either in accordance with the process variant a) or in accordance with the process variant b1)/b2) or in accordance with the process variant c) and reacting the compound thus obtainable of the formula I, in which A is chlorine, if desired in the presence of a base, with the known compound 3-methyl-4-nitroimino-perhydro-1,3,5-oxadiazine or with the known tautomeric compound 3-methyl-4-nitroamino-2,3-dihydro-6H-1,3,5-oxadiazine, respectively, to give the compound of the formula I, in which A is 3-methyl-4-nitroimino-perhydro-1,3,5-oxadiazin-5-yl;

to the compounds of the formulae II and III; to the use thereof; and to a process for the preparation thereof.

The general terms used above and below, unless defined otherwise, are as defined below.

Suitable leaving groups X are, for example, $C_1$–$C_6$alkoxy, halo-$C_1$–$C_6$alkoxy, $C_1$–$C_6$alkanoyloxy, $C_1$–$C_6$alkylthio, halo-$C_1$–$C_6$alkylthio, $C_1$–$C_6$alkylsulfonyloxy, halo-$C_1$–$C_6$alkylsulfonyloxy, phenylsulfonyloxy, tolylsulfonyloxy or halogen, preferably halogen, particularly bromine, or preferably chlorine.

Suitable dehydrating agents are, for example, thionyl chloride, triphenylphosphine/triethylamine, triphenylphosphine/azodicarboxylic ester, phosphorus oxytrichloride, phosphorus oxytrichloride/amine base, phosgene, phosgene/triethylamine, diphosgene, diphosgene/triethylamine, triphosgene, triphosgene/triethylamine, di-2-pyridylsulfite, benzenesulfonyl chloride, toluenesulfonyl chloride or toluenesulfonyl chloride/quinoline, preferably thionyl chloride or phosphorus oxytrichloride, in particular thionyl chloride.

Suitable halogenating agents are, for example, elemental chlorine, thionyl chloride, poly(sulfur dichloride), sulfur dichloride, sulfuryl chloride, phosphorus trichloride, phosphorus pentachloride or mixtures of two or more than two of these compounds, preferably thionyl chloride, sulfur dichloride or a mixture of these two compounds, particularly sulfur dichloride or a mixture of thionyl chloride and sulfur dichloride.

Suitable sulfurizing agents are, for example, elemental sulfur, poly(sulfur dichloride) or sulfur dichloride, preferably sulfur dichloride.

Preferably, reagents are used which simultaneously act as halogenating agents and sulfurizing agents, such as poly(sulfur dichloride) or sulfur dichloride, preferably sulfur dichloride.

The reactions described above and below are carried out, as required, in the absence or presence of a suitable solvent or diluent or a mixture of the same, with cooling, at room temperature or with heating, for example in a temperature range from about −80° C. to the boiling temperature of the reaction medium, preferably from about −60° C. to about +200° C., in a closed vessel, under atmospheric, elevated or reduced pressure, in an inert-gas atmosphere and/or under anhydrous conditions. Particularly advantageous reaction conditions are described below and can be taken, in particular, from the preparation examples.

Variant a)

The reaction partners can be reacted with one another without addition of a solvent or diluent. However, the addition of an inert solvent or diluent or a mixture of the same can also be advantageous, its amount not being critical. Examples of solvents or diluents of this type are in particular: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphorotriamide; nitriles, such as acetonitrile or propionitrile; and sulfoxides, such as dimethyl sulfoxide. Preferably, the reaction is carried out without addition of an inert solvent or diluent, but in the presence of a, preferably great, excess of the dehydrating agent, if this is liquid at the reaction temperature.

The reaction can be carried out, if desired, in the presence of a base as catalyst. Suitable bases for facilitating the reaction are, for example, alkali metal hydroxides or alkaline earth metal hydroxides, alkali metal hydrides or alkaline earth metal hydrides, alkali metal amides or alkaline earth metal amides, alkali metal alkanolates or alkaline earth metal alkanolates, alkali metal acetates or alkaline earth metal acetates, alkali metal carbonates or alkaline earth metal carbonates, alkali metal dialkylamides or alkaline earth metal dialkylamides or alkali metal alkylsilylamides or alkaline earth metal alkylsilylamides, alkylamines, alkylenediamines, free or N-alkylated, saturated or unsaturated cycloalkylamines, basic hetero-cycles, ammonium hydroxides or carbocyclic amines. Examples of such bases as sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calcium hydride, triethylamine, diisopropyl-ethyl-amine, triethylendiamine, cyclohexylamine, N -cyclohexyl-N,N-dimethyl-amine, N,N-diethylaniline, pyridine, 4-(N,N-dimethylamino) pyridine, quinuclidine, N-methylmorpholine, benzyl-trimethyl-ammonium hydroxide and 1,8-diazabicyclo[5.4.0] undec-7-ene (DBU).

The reaction can also be carried out in a two-phase mixture, for example a mixture of an organic solvent and an aqueous solution of a base, if desired in the presence of a phase transfer catalyst, for example a crown ether or a tetraalkylammonium salt.

The reaction is advantageously performed in a temperature range from about 0° C. to about 150° C., preferably from about 20° C. to about 100° C., preferably at the reflux temperature of the reaction mixture.

The molar ratio, in which the compound II and the sulfurizing agent are used in the reaction and which is defined by the quotient "number of moles of compound II/number of moles of sulfurizing agent", is, in particular, between 0.5 and 1, preferably between 0.75 and 1, in particular between 0.9 and 1. The dehydrating agent is preferably used in great excess.

The reaction is preferably performed at atmospheric pressure.

The reaction time is not critical; the preferred reaction time is from about 1 to about 48 hours, in particular from about 12 to about 30 hours.

The product is isolated by conventional methods, for example by filtration, crystallization, distillation or chromatography or any suitable combination of these processes.

The yield which can be achieved is generally good. A yield of more than 40% of the theoretical yield is achieved.

Preferred conditions for the reaction are described in Example H1.
Variant b1)

The reaction partners can be reacted with one another as such, i.e. without addition of a solvent or diluent, for example in the melt. However, for the most part, the addition of an inert solvent or diluent or a mixture of the same is advantageous, its amount not being critical. Examples of solvents or diluents of this type are those which are listed under variant a). Preferably, the reaction is carried out in an amide, particularly in N,N -dimethylformamide.

The reaction can be carried out, if desired, in the presence of a base as catalyst, for example of the type listed under variant a).

The reaction can also be carried out in a two-phase mixture, for example a mixture of an organic solvent and an aqueous solution of a base, if desired in the presence of a phase transfer catalyst, for example a crown ether or a tetraalkylammonium salt.

The reaction is advantageously performed in a temperature range from about −80° C. to about +60° C., preferably from about −50° C. to about +40° C.

The molar ratio, in which the compound II and the dehydrating agent are used in the reaction and which is defined by the quotient "number of moles of compound II/number of moles of dehydrating agent", is, in particular, between 0.5 and 1, preferably between 0.75 and 1, in particular between 0.9 and 1.

The reaction is preferably performed at atmospheric pressure.

The reaction time is not critical; the preferred reaction time is from about 1 to about 24 hours, in particular from about 5 to about 15 hours.

The product is isolated by conventional methods, for example by filtration, crystallization, distillation or chromatography or any suitable combination of these processes.

The yield which can be achieved is generally very good. A yield of more than 80% of the theoretical yield is achieved.

Preferred conditions for the reaction are described in Example H2.
Variant b2)

The reaction partners can be reacted with one another as such, i.e. without addition of a solvent or diluent, for example in the melt. However, for the most part, the addition of an inert solvent or diluent or a mixture of the same is advantageous, its amount not being critical. Examples of solvents or diluents of this type are those which are listed under variant a). Preferably, the reaction is carried out in a halogenated hydrocarbon, such as di- or, in particular, tetrachloromethane.

The reaction can be carried out, if desired, in the presence of a base as catalyst, for example of the type listed under variant a).

The reaction can also be carried out, if desired, in the presence of an acid as catalyst. Acids which are suitable for this purpose are, for example, strong organic carboxylic acids, such as unsubstituted or substituted, for example by halogen, $C_1$–$C_4$alkanecarboxylic acids, for example formic acid, acetic acid or propionic acid, sulfonic acids, such as methylsulfonic acid, p-toluenesulfonic acid or camphor-10-sulfonic acid, Lewis acids, such as boron trifluoride-diethyl ether complexes or boron trifluoride-dimethyl ether complexes, and mineral acids, such as sulfuric acid, hydrochloric acid or phosphoric acid.

The reaction can also be carried out in a two-phase mixture, for example a mixture of an organic solvent and an aqueous solution of a base or acid, if desired in the presence of a phase transfer catalyst, for example a crown ether or a tetraalkylammonium salt.

The reaction is advantageously performed in a temperature range from about −50° C. to about +160° C., prefeably from about −20° C. to about +60° C.

The molar ratio, in which the compound III and the sulfurizing agent are used in the reaction and which is defined by the quotient "number of moles of compound III/number of moles of sulfurizing agent", is, in particular, between 0.5 and 1, preferably between 0.75 and 1, in particular between 0.85 and 0.95.

The reaction is preferably performed at atmospheric pressure.

The reaction time is not critical; the preferred reaction time is from about 1 to about 24 hours, in particular from about 1 to about 15 hours.

The product is isolated by conventional methods, for example by filtration, crystallization, distillation or chromatography or any suitable combination of these processes.

The yield which can be achieved is generally good. A yield of more than 50% of the theoretical yield can be achieved.

Preferred reaction conditions are described in Example H4.

Variant c)

(i) Reaction of the Compounds IV and V $C_1$–$C_6$alkoxy is either straight-chain, i.e. methoxy, ethoxy, propoxy, butoxy, pentyloxy or hexyloxy, or branched, for example isopropoxy, isobutoxy, sec-butoxy, tert-butoxy, isopentyloxy, neopentyloxy or isohexyloxy.

$C_1$–$C_6$alkyl is either straight-chain, i.e. methyl, ethyl, propyl, butyl, pentyl or hexyl, or branched, for example isopropyl, isobutyl, sec-butyl, tert-butyl, isopentyl, neopentyl or isohexyl.

Preference is given to compounds V, in which $R_1$ and $R_2$ together are oxo and $R_3$ is $C_1$–$C_6$alkoxy, preferably $C_1$–$C_4$alkoxy, in particular methoxy or especially ethoxy.

The reaction partners can be reacted with one another without addition of a solvent or diluent. However, the addition of an inert solvent or diluent or a mixture of the same can also be advantageous, its amount not being critical. Examples of solvents or diluents of this type are those which are listed under variant a). Preferably, the reaction is carried out without addition of an inert solvent or diluent.

The reaction is advantageously performed in a temperature range from about 0° C. to about 180° C., preferably from about 40° C. to about 150° C., preferred at the reflux temperature of the reaction mixture.

The molar ratio, in which the compounds IV and V are used in the reaction and which is defined by the quotient "number of moles of compound IV/number of moles of compound V" is, in particular, between 0.1 and 1, preferably between 0.4 and 1, in particular between 0.5 and 0.8.

The reaction is preferably performed at atmospheric pressure.

The reaction time is not critical; the preferred reaction time is from about 1 to about 48 hours, in particular from about 5 to about 15 hours.

The product is isolated by conventional methods, for example by filtration, crystallization, distillation or chromatography or any suitable combination of these processes.

The yield which can be achieved is generally very good. A yield of more than 75% of the theoretical yield is achieved.

Preferred conditions for the reaction are described in Example H3.

(ii) Reaction of the Compounds II to Give the Compound I, in which A is Chlorine The reaction of the compounds II obtainable according to step (i) to give the compound I, in which A is chlorine, according to the variant c) is performed either as described under the variant a) or as described under the variant b1)/b2).

Variant d)

The preparation of the compound I, in which A is chlorine, according to the variant d) is performed either in accordance with the variant a) or in accordance with the variant b1)/b2) or in accordance with the variant c).

The reaction of the compound thus obtainable of the formula I, in which A is chlorine, with 3-methyl-4-nitroimino-perhydro-1,3,5-oxadiazine or the tautomeric 3-methyl-4-nitroamino-2,3-dihydro-6H-1,3,5-oxadiazine, respectively, to give the compound 1, in which A is 3-methyl-4-nitroimino-perhydro-1,3,5-oxadiazin-5-yl, according to the variant d) can be performed in such a manner, that the reaction partners are reacted with one another as such, i.e. without addition of a solvent or diluent, for example in the melt. However, for the most part, the addition of an inert solvent or diluent or a mixture of the same is advantageous, its amount not being critical. Examples of solvents or diluents of this type are those which are listed under variant a). Preferably, the reaction is carried out in an amide, particularly in N,N-dimethylformamide.

The reaction can be carried out, if desired, in the presence of a base as catalyst, for example of the type listed under variant a).

The reaction is advantageously performed in a temperature range from about −20° C. to about +180° C., preferably from about +10° C. to about +100° C.

The reaction is preferably performed at atmospheric pressure.

The reaction time is not critical; the preferred reaction time is from about 1 to about 24 hours, in particular from about 3 to about 12 hours.

The product is isolated by conventional methods, for example by filtration, crystallization, distillation or chromatography or any suitable combination of these processes.

The yield which can be achieved is generally very good. A yield of more than 65% of the theoretical yield is achieved.

Preferred conditions for the reaction are described in Example H5.

The compounds II and III are novel and are likewise subject-matter of the invention.

Preferred compounds II and III are those, in which X is halogen, especially bromine or in particular chlorine.

The process for preparing the compounds II and III is likewise subject-matter of the invention. The compounds II can be prepared, for example, as described under variant c), i.e. by reacting a compound IV with a compound V. The compounds III can be prepared, for example, as described under variant b1), i.e. by reacting a compound II with a dehydrating agent.

The use of the compounds II as intermediates in the process of the invention for preparing the compounds III or the compounds I and the use of the compounds III as intermediates in the process of the invention for preparing the compounds I are likewise subject-matter of the invention.

The invention relates to all those embodiments of the process, in which one starts from a compound, which can be used as a starting product or intermediate at any stage of the process, and carries out all or some of the missing steps, or in which one uses, or, in particular, forms under the reaction conditions, a starting material in the form of a derivative or salt and/or of its racemates or antipodes.

The invention relates in particular to the process described in the Examples H1 to H5.

Starting materials and intermediates used according to the invention for the preparation of the compounds I which are novel, a process for the preparation thereof and the use thereof as starting materials and intermediates for the preparation of the compounds I are likewise subject-matter of the invention; this relates in particular to the compounds II and III.

The compounds I are valuable intermediates in the process of preparing pesticidal, especially insecticidal or acaricidal, formulations.

The following examples illustrate the invention. They do not restrict the invention. Temperatures are given in degrees Celsius. The abbreviation "h" means hours.

Preparation Examples

EXAMPLE H1

2-chloro-5-chloromethyl-thiazole

A mixture of 10.5 ml of thionyl chloride, 0.5 g of N-(2-chloroallyl)formamide and 0.44 g of sulfur dichloride is refluxed for 24 h. The reaction mixture is then concentrated on a rotary evaporator, and the residue is purified by flash chromatography on silica gel (mobile phase: dichloromethane). The title compound is obtained in this manner in a yield of 42% (melting point: 35°).

EXAMPLE H2

2-chloroallylisonitrile

A solution of 2.5 g of thionyl chloride in 6 ml of N,N-dimethylformamide is added dropwise, with stirring, to a solution of 2.4 g of N-(2-chloroallyl)formamide in 40 ml of N,N-dimethylformamide, after cooling to −50°. 4.7 g of sodium carbonate are then added. The reaction mixture is stirred for 12 h at room temperature, diluted with 100 ml of water and extracted with pentane. The pentane extract dried over sodium sulfate gives the title compound, after distilling off the pentane at atmospheric pressure, in a yield of 81% and in a purity of more than 80% (impurity: N,N-dimethylformamide). The title compound can be further used without additional purification.

EXAMPLE H3

N-(2-chloroallyl)formamide

A mixture of 37.2 g of 2-chloroallylamine and 43.7 g of ethyl formate is refluxed for 12 h. The reaction mixture is then concentrated on a rotary evaporator, and the residue is fractionally distilled under reduced pressure via a Vigreux column. The title compound is obtained in this manner (boiling point: 131° at 19 mbar; yield: 79%).

EXAMPLE H4

2-chloro-5-chloromethylthiazole a) 0.57 g of sulfur dichloride is added dropwise to a solution of 0.5 g of 2-chloroallyl isonitrile in 7.5 ml of tetrachloromethane at 0°. The reaction mixture is stirred for 4 h at 40°, the solvent is distilled off at atmospheric pressure and the residue is subjected to Kugelrohr distillation (20 mbar, 120–130°). The pure title compound is obtained in this manner in a yield of 12%.

b) 0.4 g of thionyl chloride is added dropwise to a solution of 0.5 g of 2-chloroallylisonitrile in 7.5 ml of tetrachloromethane at 0°. After 5 minutes, 0.57 g of sulfur dichloride is added dropwise at 0°. The reaction mixture is stirred for 12 h at room temperature, the solvent is distilled off under atmospheric pressure, and the residue is subjected to a Kugelrohr distillation (20 mbar, 120–130°). The pure title compound is obtained in this manner in a yield of 52%.

EXAMPLE H5

5-(2-Chlorothiazol-5-ylmethyl)-3-methyl-4-nitroimino-perhydro-1,3,5-oxadiazine

A mixture of 1.62 g of 3-methyl-4-nitroimino-perhydro-1,3,5-oxadiazine, 2.44 g of 2-chloro-5-chloromethyl-thiazole, 4.2 g of potassium carbonate and 25 ml of N,N-dimethylformamide is heated for 5 h at 60° and then filtered. The filtrate is evaporated in vacuo on a rotary evaporator, and the residue is purified by chromatography [silica gel; dichloromethane/methanol (95:5)]. This gives the title compound, which melts at 132–134°, in a yield of 67%.

What is claimed is:
1. A process for preparing a compound or the formula

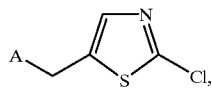

I in which A is chlorine of 3-methyl-4-nitroimino-perhydro-1,3,5-oxadiazin-5-yl, which process comprises
  a) reacting a compound of the formula

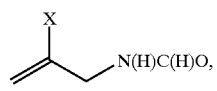

II in which X is a leaving group, optionally in the presence of a base, with a dehydrating agent, a halogenating agent, and a sulfurizing agent, to give the compound of the formula I, in which A is chlorine, or
  b1) reacting a compound of the formula II, optionally in the presence of a base, with a dehydrating agent to give a compound of the formula

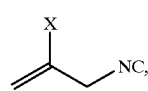

III in which X is as defined for the formula II, and
  b2) reacting the compound thus obtainable of the formula III with a halogenating agent and a sulfurizing agent, optionally in the presence of a base or acid, to give the compound of the formula I, in which A is chlorine, or c) reacting a compound of the formula

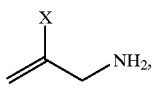
IV in which X is as defined for the formula II, with a compound of the formula

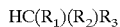
V, in which either $R_1$ and $R_2$ together are oxo and $R_3$ is hydroxy, $C_1$–$C_6$alkoxy or $N(R_4)R_5$, $R_4$ and $R_5$ being, independently of one another, hydrogen or $C_1$–$C_6$alkyl, or $R_1$, $R_2$ and $R_3$, independently of one another, are $C_1$–$C_6$alkoxy, to give a compound of the formula II and reacting the compound thus obtainable of the formula II either in accordance with the process variant a) or in accordance with the process variant b1)/b2) to give the compound of the formula I, in which A is chlorine, or d) preparing the compound of the formula I, in which A is chlorine, either in accordance with the process variant a) or in accordance with the process variant b1)/b2) or in accordance with the process variant c) and reacting the compound thus obtainable of the formula I, in which A is chlorine, optionally in the presence of a base, with 3-methyl-4-nitroimino-perhydro-1,3,5-oxadiazine or with 3-methyl-4-nitroamino-3,3-dihydro-6H-1,3,5-oxadiazine, to give the compound of the formula I, in which A is 3-methyl-4-nitroimino-perhydro-1,3,5-oxadiazin-5-yl.

2. The process according to claim 1 for preparing the compound of the formula I, in which A is chlorine, wherein a compound of the formula II, in which X is a leaving group, is reacted, optionally in the presence of a base, with a dehydrating agent, a chlorinating agent and a sulfurizing agent.

3. A process according to claim 2, wherein a compound of the formula II is used, in which X is chlorine.

4. A process according to claim 2, wherein the dehydrating agent is thionyl chloride.

5. The process according to claim 2 wherein the chlorinating agent is thionyl chloride or sulfur dichloride.

6. The process according to claim 2 wherein the sulfurizing agent is sulfur dichloride.

7. A process according to claim 4, wherein thionyl chloride is used in excess.

8. A process according to claim 7, wherein the reaction is carried out at the reflux temperature of the reaction mixture.

9. The process according to claim 6, wherein the molar ratio in which the compound II and the sulfurizing agent are used is between 0.5 and 1.

* * * * *